United States Patent [19]
Lockhart

[11] Patent Number: 5,241,710
[45] Date of Patent: Sep. 7, 1993

[54] SANITARY PANTY

[76] Inventor: Janice T. Lockhart, 2736 Yorktown, Laplace, La. 70068

[21] Appl. No.: 971,220

[22] Filed: Nov. 4, 1992

[51] Int. Cl.$^5$ .............................................. A41B 9/04
[52] U.S. Cl. .......................................... 2/406; 2/400;
2/408; 450/103; 604/385.1; 604/395; 604/396
[58] Field of Search .................... 2/400, 401, 402, 403, 2/406, 408, 409; 604/395, 396, 397, 398, 399, 385.1; 450/102, 103, 104

[56] References Cited

U.S. PATENT DOCUMENTS

| | | | |
|---|---|---|---|
| 387,159 | 7/1888 | Grossmann | 604/395 |
| 1,773,442 | 8/1930 | Speh | 2/94 |
| 2,595,507 | 5/1952 | Beck | 604/395 |
| 3,224,448 | 4/1963 | Diebold | |
| 4,022,212 | 5/1977 | Lovison | 604/395 |
| 4,221,221 | 9/1980 | Ehrlich | 604/385.1 X |
| 4,280,230 | 7/1981 | LaFleur | |
| 4,597,110 | 7/1986 | Smith, Sr. et al. | |
| 4,675,918 | 6/1987 | O'Brien | |
| 4,738,678 | 4/1988 | Paulis | 604/385.1 |
| 4,743,240 | 5/1988 | Powell | 604/385.1 |
| 4,835,795 | 6/1989 | Lonon | |
| 4,961,419 | 10/1990 | Tribble et al. | 2/403 X |
| 4,964,859 | 10/1990 | Feldman | 206/440 X |
| 5,070,869 | 12/1991 | Zhang | 2/403 X |
| 5,093,935 | 3/1992 | Countee, Jr. | 2/403 X |

FOREIGN PATENT DOCUMENTS

| | | | |
|---|---|---|---|
| 25493/57 | 2/1957 | Australia | |
| 0436766 | 3/1949 | Italy | 604/395 |
| 0497591 | 12/1938 | United Kingdom | 450/103 |

Primary Examiner—Clifford D. Crowder
Assistant Examiner—Jeanette E. Chapman
Attorney, Agent, or Firm—Richard C. Litman

[57] ABSTRACT

A two piece panty with one of the pieces being a removable lower or crotch portion. This portion has an inner section designed for the absorption of menses, and an outer moisture resistant backing that includes both a front and rear engaging means and a pocket adapted to hold a pre-wrapped moistened towelette. Thus, when the inner section becomes soiled, it is easily replaceable by disengaging the crotch portion and replacing it with a new one.

8 Claims, 2 Drawing Sheets

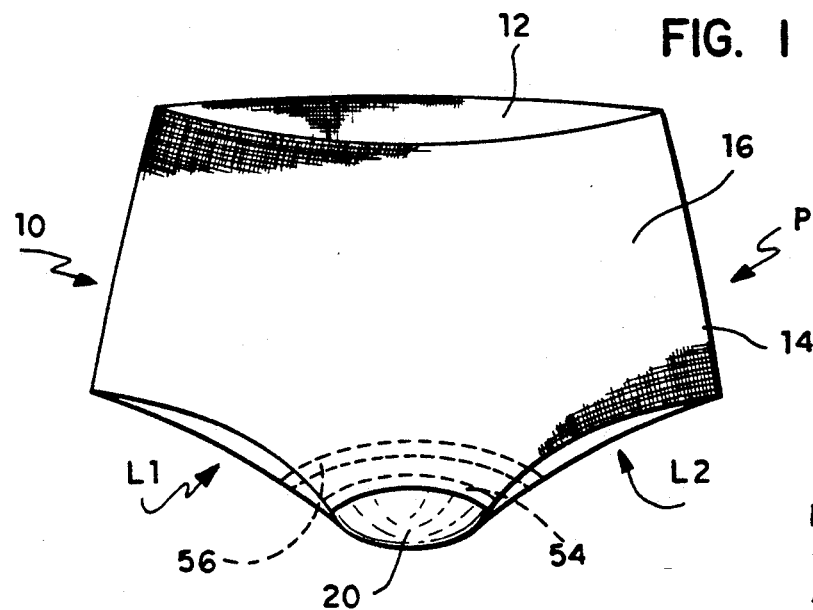
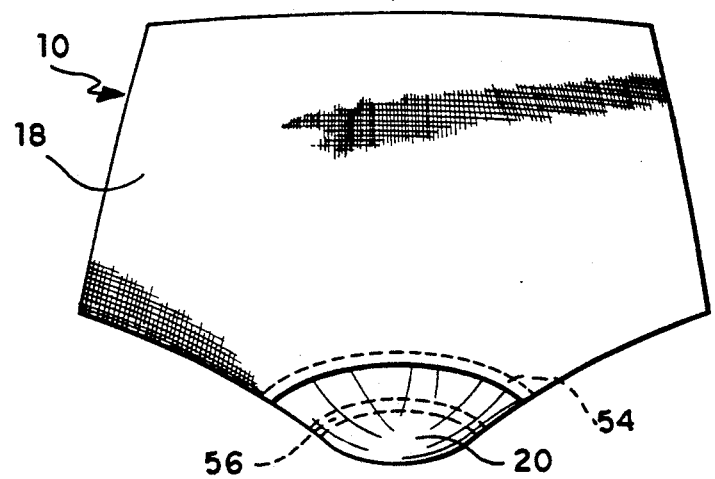
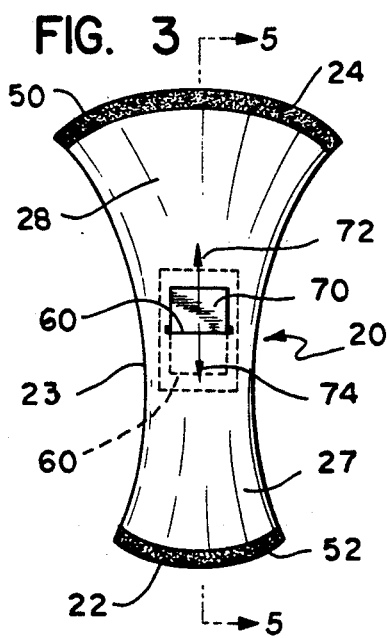
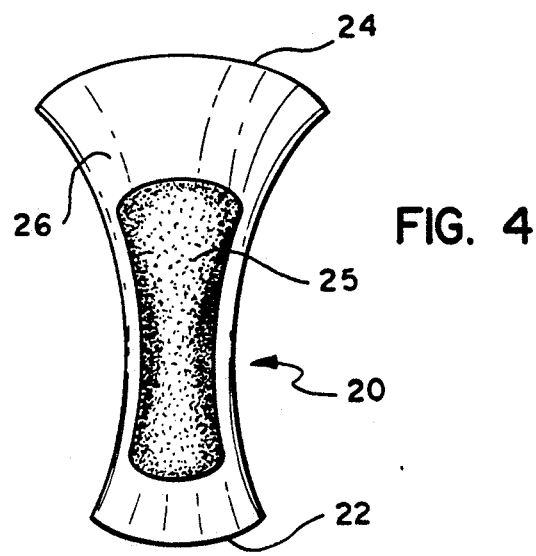

SANITARY PANTY

BACKGROUND OF THE INVENTION

1. Field of the Invention

The present invention relates to garments. More specifically, it relates to undergarments. Even more specifically, it relates to women's panties where there is a removably engageable crotch area that includes a disposable absorption means, viz. a sanitary napkin or the like that further includes a pre-wrapped moistened towelette packaged in a pocket located in a non-absorbent plastic backing on the outer surface of the removable crotch area, for use during menstruation.

2. Description of the Prior Art

A number of patents have been issued which disclose undergarments or panties where the crotch area is completely or partially removable.

For example, in Australian Application 25,493/57, published on Sep. 26, 1957; the applicant being George Robert Collins, there is disclosed women's panties with a detachable gusset. In the reference to the drawings, specifically FIGS. 2 and 3, buttons are shown on the main portion of the garment and button holes are discussed as disposed on the detachable portion.

Secondly, U.S. Pat. No. 3,224,448 issued on Dec. 21, 1965 to George L. Diebold discloses a separable crotch undergarment. This invention has a one-piece body portion including a pair of depending leg portions. The separable crotch portion of the device consists of two elongated, generally rectangular sections of material. These two sections overlap and will normally maintain the crotch closed with normal movement of the user.

Another similar patent is U.S. Pat. No. 4,280,230 issued on Jul. 28, 1981 to Ruby S. LaFleur that discloses disposable training panties. A cotton pants member has a disposable paper crotch insert that fits into a cut-out crotch opening. The disposable crotch insert has perforations to receive hooks of a VELCRO-like fastener that is disposed on flaps attached to the cotton pants member.

Another patent of interest is U.S. Pat. No. 4,597,110 issued on Jul. 1, 1986 to Jams R. Smith, Sr. et al. This patent discloses an undergarment with a waistband and a body element. The body element has a back pane, a front panel, and leg openings. A crotch segment extends from the lower central portion of the back panel and continues to a terminus at a distal front or upper edge. There are first and second fastener means, preferably of a hook and loop type, disposed on the terminus of the crotch segment and the complimentary distal lower edge at the central lower portion of the front panel.

In another related patent, U.S. Pat. No. 4,675,918 issued on Jun. 30, 1987 to Ann O'Brien discloses a one piece brief with hook and pile closures. There is an upper band portion with an upper horizontal edge, a front panel and a rear panel. The front and rear panels include first and second vertical side edges. Attached to the front panel is a short tab portion. Likewise, attached to the rear panel is a long crotch portion. There are vertical lengths of fastening tape attached to the first and second vertical side edges. Attached to the termini of the short tab portion and the long crotch portion are horizontal lengths of fastening tape. The tape is discussed as being preferably of the hook and loop type.

Finally U.S. Pat. No. 4,835,795 issued on Jun. 6, 1989 to Edward M. Lonon discloses a body suit and underpants with self-gripping fasteners. The garment has a front body portion and a back body panel extending from the back body panel is a flap that terminates on the inside of its front end with a VELCRO strip. There is a similarly dimensioned strip of complimenting VELCRO secured to the center of the front body panel.

None of the above inventions and patents, taken either singly or in combination, is seen to describe the instant invention as claimed.

SUMMARY OF THE INVENTION

The current invention is a two piece panty with one of the pieces being a removable lower or crotch portion. This portion has an inner section designed for the absorption of menses, and an outer moisture resistant backing that includes both a front and rear engaging means and a pocket to hold a pre-wrapped moistened towelette. Thus, when the inner section becomes soiled, it is easily replaceable by disengaging the crotch portion and replacing it with a new one. The towelette can be used to clean the crotch area or the soiled hands of the user if desired.

Accordingly, it is a principal object of the invention to provide a two piece panty for use during menstruation where the user can quickly and easily change the soiled pad.

It is another object of the invention to provide a pre-moistened towelette contained integrally within the removable portion of the two piece panty to allow the user to clean themselves if desired during the changing process.

It is a further object of the invention to provide an alternative to existing feminine hygiene products that some users find uncomfortable or unnecessarily bulky.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 1 is front perspective view of the present invention.

FIG. 2 is a rear elevational view.

FIG. 3 is a bottom view of the removable crotch section with broken lines showing the pocket that contains the prepackaged towelette.

FIG. 4 is a top view of the removable crotch section showing the absorbent member.

Similar reference characters denote corresponding features consistently throughout the attached drawings.

DETAILED DESCRIPTION OF THE PREFERRED EMBODIMENT

Figure 5:
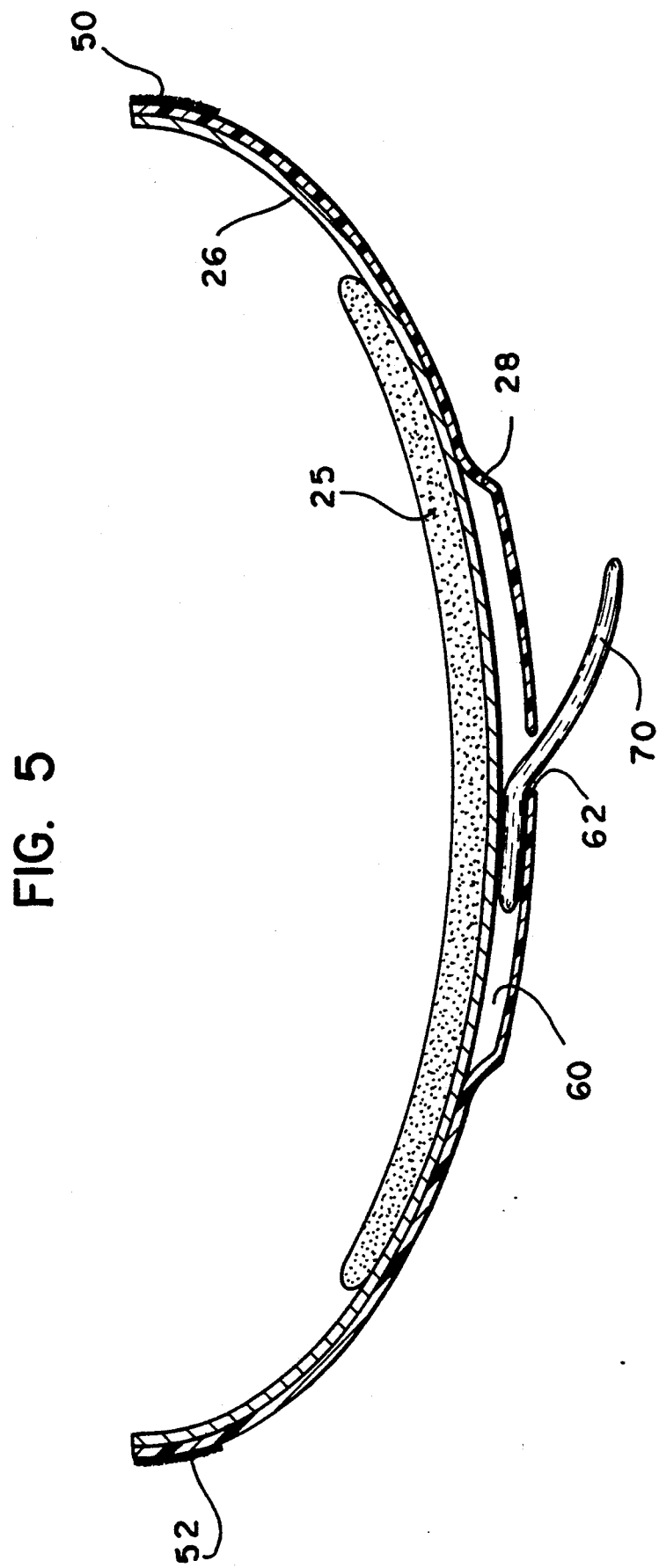
FIG. 5 is a cross sectional view of the removable crotch section taken along line 5—5 of FIG. 3.

Referring to FIGS. 1 and 2, the sanitary panty P is shown with the removable crotch section 20 in place. The body element 10 has an inner surface 12, an outer surface 14, a front panel 16, a rear panel 18, and two leg openings L1 and L2. The body element 10 would preferably be made of a material such as cotton. The removable crotch section 20 is located in between the two leg openings L1 and L2. Referring to FIGS. 3, 4, and 5, the removable crotch section has a front end 22, a rear end 24, an absorptive pad 25 on the side 26 adjacent to the user's body, and a moisture resistant exterior liner 27 on the opposite side 28. The front end 22 and the rear end 24 both have fastening means 50, 52 that engage with complementary areas 54, 56 on, respectively, the front and rear panels of the body element 10. Referring now to FIGS. 3 and 5, there is an pocket 60 having a slot 62 in the moisture resistant exterior liner 28. The pocket 60 is located in the medial portion 23 of the removable crotch section 20. The pocket receives a pre-wrapped, moistened towelette 70, as shown by arrows 72 and 74, and when the towelette 70 is fully inserted in the pocket 60, the slot 62 can close so that the towelette 70 does not protrude. The towelette 70 is of a type well known in the art, moistened with water or a mild antiseptic solution that would not irritate mucous membranes. The packaging of the towelette 70 would be sufficiently light and flexible to be substantially unnoticeable to the wearer when either walking or sitting. The construction of the pocket 60 in the moisture resistant liner 28 could be provided by having the moisture resistant liner 28 being double walled throughout, with an adhesive seal or the like surrounding the area that defines the pocket 60 and the slot G2 being out into the outer wall. Optionally, the moisture resistant liner 28 could be double walled or folded to provide the pocket GO and the slot 62. The actual material used for the moisture resistant liner 28 could be any we known plastic material. The inner 28, to provide for comfort, would preferably have a lining on the side 2G made of a suitably soft material. The fastening means 50, 52 and their engaging areas 54, 56 are preferably of the hook and loop type but the types could be substituted, such as snaps, buttons, hook and eye, or zip closure locking seams. The absorptive pad 25 could be made of any appropriate material well known in the art.

It is to be understood that the present invention is not limited to the sole embodiment described above, but encompasses any and all embodiments within the scope of the following claims.

I claim:

1. A panty for use by women during menstruation comprising:
   a) a body element including a front panel, a rear panel, two leg openings, an interior, and an exterior;
   b) a removable crotch portion having a front end and a rear end, a median portion, and including an absorptive interior pad, a moisture resist at exterior line further including means to define an opening adapted to receive a pre-wrapped, moistened towelette, said means defining an opening being a slit located proximate said median portion of said removable crotch portion, and front and rear engagement extensions located on said front end and said rear end;
   c) a fastening means to removal by engage each of said engagement extensions of said removably crotch portion with said front panel and said rear panel; whereby
   when desired, for example fi soiled, said removable crotch portion can be easily removed from said body element, said towelette can be removed form said opening, used to clean an area of the body and then can be discarded with said crotch portion.

2. The panty according to claim 1 where said fastening means is of the hook and loop type.

3. The panty according to claim 1 where said fastening means is of the hook and eye type.

4. The panty according to claim 1 where said fastening means is a snap.

5. The panty according to claim 1 where said fastening means is a button.

6. The panty according to claim 1 where said towelette is prepackaged in its own moisture proof wrapping and said means to define an opening comprises a pocket surrounding said towelette wrapping.

7. The panty according to claim 6 where said means to define an opening further includes a slot suitably wide for easily removing said towelette wrapping from said crotch portion.

8. The panty according to claim 6 where said pocket is made up of said moisture proof exterior liner.

* * * * *

UNITED STATES PATENT AND TRADEMARK OFFICE
CERTIFICATE OF CORRECTION

PATENT NO. : 5,241,710
DATED : September 7, 1993
INVENTOR(S) : Ms. Janice T. Lockhart It is certified that error appears in the above-indentified patent and that said Letters Patent is hereby corrected as shown below:

```
Col. 1, line 45 change "pane" to --panel--.
Col. 3, line 25 change "G2" to --62--.
Col. 3, line 27 change "GO" to --60--.
Col. 3, line 29 change "we" to --well--.
Col. 3, line 31 change "2G" to --26--.
Col. 3 line 30 change "inner" to --liner--.

Column 4,
In Claim 1, line 8 change "resistat" to --resistant--.
In Claim 1, line 9 change "line" to --liner--.
In Claim 1, line 20 change "fi" to --if--.
In Claim 1, line 22 change "form" to --from--.
```

Signed and Sealed this

Seventh Day of June, 1994

Attest:

BRUCE LEHMAN

*Attesting Officer*     *Commissioner of Patents and Trademarks*